(12) United States Patent
Rich

(10) Patent No.: US 11,737,904 B2
(45) Date of Patent: Aug. 29, 2023

(54) CUSTOM MULTI-LAYERED ORTHOTIC/ORTHOSIS, AND METHOD FOR FORMING

(71) Applicant: Jeffrey S. Rich, Forest Hills, NY (US)

(72) Inventor: Jeffrey S. Rich, Forest Hills, NY (US)

(73) Assignee: MASTERFIT ENTERPRISES, INC., Briarcliff Manor, NY (US)

( * ) Notice: Subject to any disclaimer, the term of this patent is extended or adjusted under 35 U.S.C. 154(b) by 1008 days.

(21) Appl. No.: 16/551,229

(22) Filed: Aug. 26, 2019

(65) Prior Publication Data
US 2019/0374369 A1 Dec. 12, 2019

Related U.S. Application Data

(62) Division of application No. 14/863,656, filed on Sep. 24, 2015, now Pat. No. 10,420,669.
(Continued)

(51) Int. Cl.
*A61F 5/14* (2022.01)
*A43B 17/00* (2006.01)
(Continued)

(52) U.S. Cl.
CPC ............... *A61F 5/14* (2013.01); *A43B 7/141* (2013.01); *A43B 7/1415* (2013.01); *A43B 17/00* (2013.01); *A43B 17/006* (2013.01)

(58) Field of Classification Search
CPC . A61F 5/0111; A61F 5/14; A43B 7/14; A43B 7/141; A43B 7/1415; A43B 17/00; A43B 17/006
See application file for complete search history.

(56) References Cited

U.S. PATENT DOCUMENTS

| | | | |
|---|---|---|---|
| 7,008,386 B2 * | 3/2006 | Alaimo | A43B 13/122 600/592 |
| 8,708,942 B2 * | 4/2014 | Kuhn | A61F 5/0127 602/23 |

(Continued)

*Primary Examiner* — Keri J Nelson
(74) *Attorney, Agent, or Firm* — McGlew and Tuttle, P.C.

(57) ABSTRACT

A multilayer orthotic/orthosis has a cover layer, a shell layer and a posting layer. The shell layer is formed of a thermoplastic having a moldable temperature. The rigidity of the shell layer, and in particular the rigidity of the thermoplastic is chosen to be of a magnitude to support the portion of the individual at temperatures below the moldable temperature. The shell layer, preferably the thermoplastic, has a flexibility above the moldable temperature to mold the shell layer into a shape to support the portion of the individual. The shell layer has two layers of woven polyester fibers ("scrim") on the top and bottom. The scrim gives the plastic strength and prevents it from stretching excessively when molding. These unique properties make the material well suited for stacking multiple layers without having excessive bulking of material top lines. Both sides of the shell layer are coated with a layer of hot melt cement/glue/adhesive for easy attachment of various layers or other materials. One side of the shell layer is connected to one side of the cover layer. A posting layer is arranged on a side of the shell layer diametrically opposite the cover layer, and provides support for the orthotic/orthosis in order to prevent rocking, especially when the orthotic/orthosis is for the foot of the individual.

20 Claims, 11 Drawing Sheets

Related U.S. Application Data

(60) Provisional application No. 62/058,322, filed on Oct. 1, 2014.

(51) Int. Cl.
*A43B 7/1415* (2022.01)
*A43B 7/1405* (2022.01)

(56) References Cited

U.S. PATENT DOCUMENTS

| | | | |
|---|---|---|---|
| 10,420,669 B2 * | 9/2019 | Rich | A43B 7/1415 |
| 2007/0004993 A1 * | 1/2007 | Coppens | A61F 5/058 |
| | | | 128/846 |

* cited by examiner

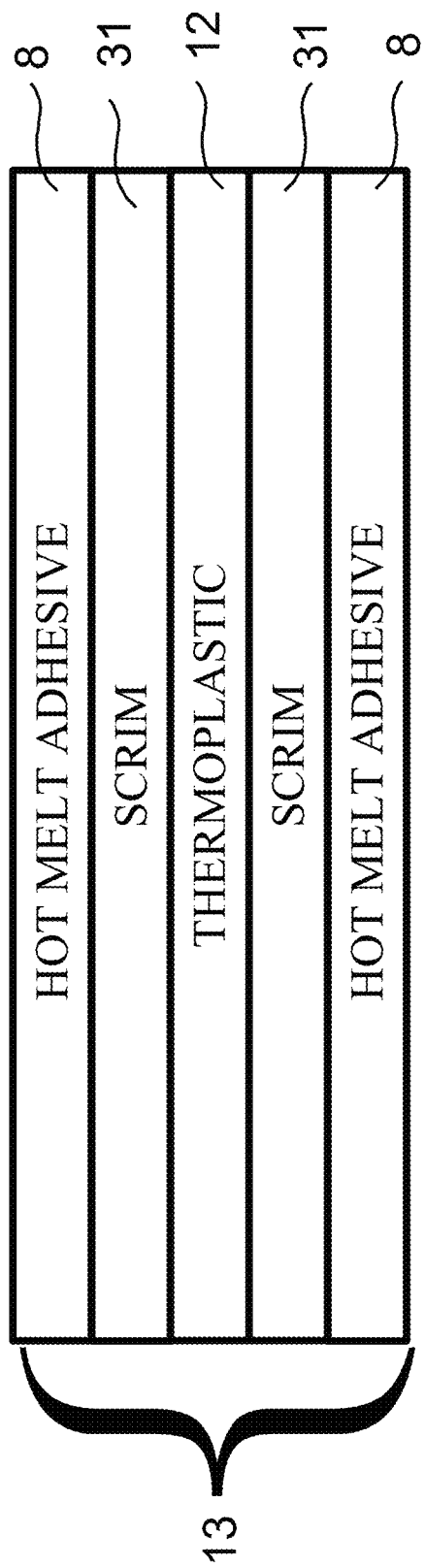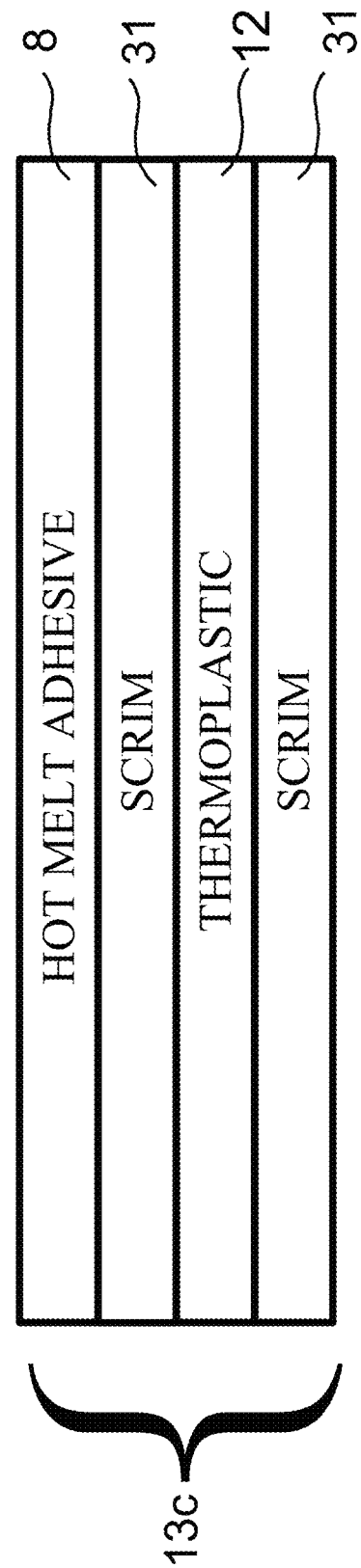

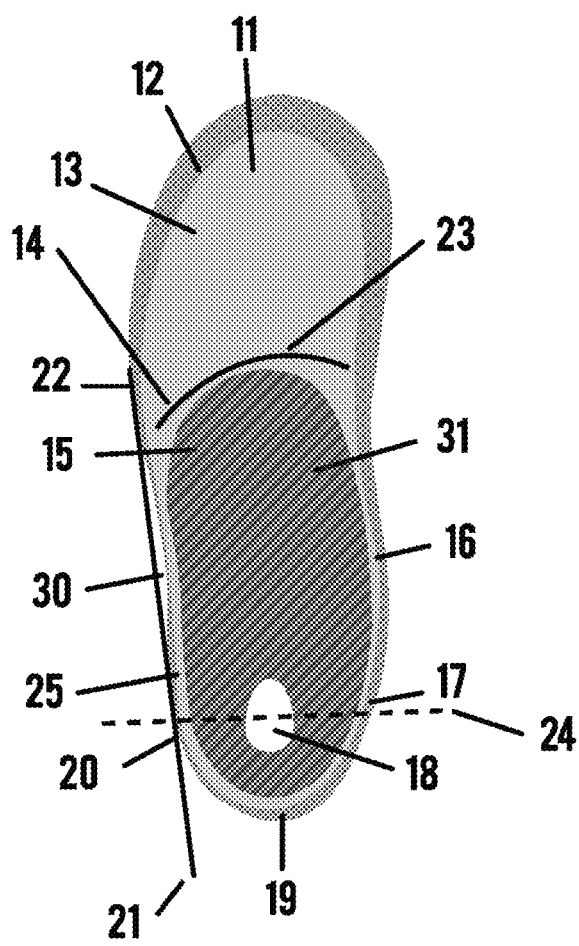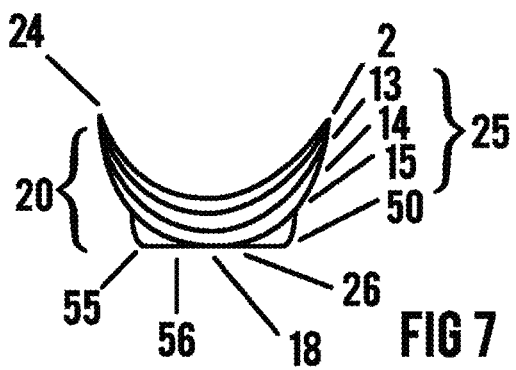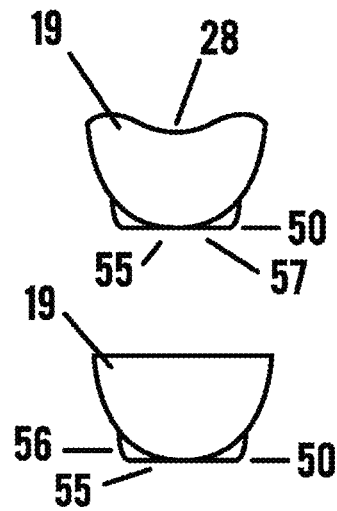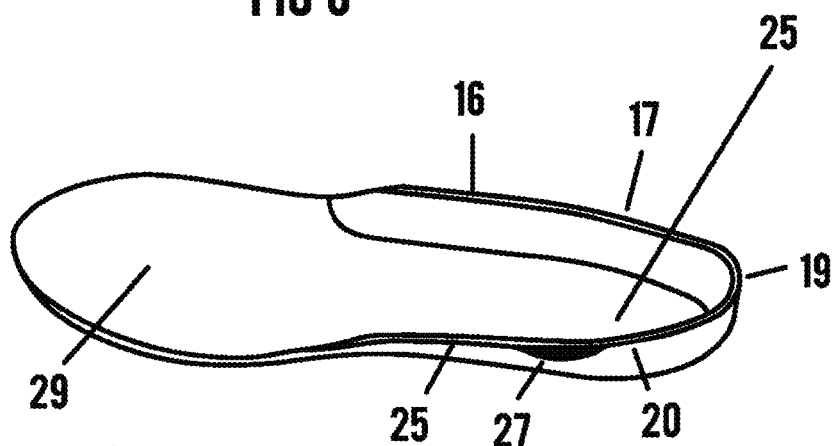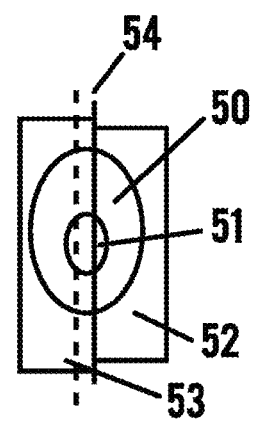
FIG 6
FIG 7
FIG 8
FIG 9
FIG 10

CUSTOM MULTI-LAYERED ORTHOTIC/ORTHOSIS, AND METHOD FOR FORMING

CROSS REFERENCE TO RELATED APPLICATIONS

This application claims the benefit of priority under 35 U.S.C. § 120 of U.S. patent application Ser. No. 14/863,656 filed Sep. 24, 2015, which claims the benefit of priority under 35 U.S.C. § 120 of U.S. Provisional Patent Application 62/058,322 filed Oct. 1, 2014, the entire contents of which are incorporated herein by reference.

FIELD OF THE INVENTION

The invention relates to an orthotic appliance/orthosis that is formed from multiple layers and customized to an individual. The invention more specifically relates to an orthotic appliance/orthosis that is for the foot and arch, preferably the heel, and where the orthotic appliance/orthosis is self stabilizing, and has self beveling edges.

BACKGROUND OF THE INVENTION

The portions of an individual that could benefit from orthotics are many, and come in many different sizes and shapes. Even the same portion of different individuals, such as the foot, come in many different sizes and shapes, and need different corrections, so that the more customized an orthotic appliance/orthosis is, the more the orthotic appliance/orthosis will benefit the individual.

Making custom orthotics requires extensive training and hand-on experience. Even after that training and experience is gained, the current processes for creating orthotics is very time consuming and is as much art as science. The process involves many steps, such as examining the foot, casting the foot to create a negative impression, pouring plaster inside the negative (to create the positive mold that the orthotic is eventually fabricated from), fine tuning the shape of the plaster positive, vacuum forming plastic and/or rubber to create the orthotic shell, posting (gluing extra material) to the heel and base to prevent rocking, and grinding the posting flat and smoothing the finish. It takes about two hours to make an orthotic using the plaster casting method.

Making a custom orthotic appliance/orthosis using the plaster casting method can be expensive. Making an orthotic appliance/orthosis which is not custom, and just uses off-the-shelf standard components, is less expensive, but often results in an orthotic appliance/orthosis which provides much less of a benefit.

SUMMARY OF THE INVENTION

The orthotic/orthosis of the present invention is for a portion of an individual, and can be for any portion of the individual that could benefit from an orthotic device/orthosis. For ease in understanding the present invention, the present invention will be described as being an orthotic device/orthosis for the foot and arch portion of an individual, and in particular for the heel portion of the foot. The multilayer orthotic/orthosis has a cover layer, a shell layer and a posting layer. It is possible for the present invention to have a plurality of shell sheets forming the shell layer, and have a reinforce stabilizer layer. The shell layer is formed of a thermoplastic having a moldable temperature. The rigidity of the shell layer, and in particular the rigidity of the thermoplastic is chosen to be of a magnitude to support the portion of the individual at temperatures below the moldable temperature. The shell layer, preferably the thermoplastic, has a flexibility above the moldable temperature to mold the shell layer into a shape to support the portion of the individual. One side of the shell layer is connected to one side of the cover layer. A posting layer is arranged on a side of the shell layer diametrically opposite the cover layer, and provides support for the orthotic/orthosis in order to prevent rocking, especially when the orthotic/orthosis is for the foot of the individual.

Another one of the features of the present invention is a unique new orthotic blank shape. Unlike the straight edge lines found on present orthotic blank shapes, the present invention uses a design that has concave hollows and negative edge lines. Materials such as the thermoplastic of the shell layer (used in the making of shoe heel counter and toe boxes), because of their low molding temperatures, allow the orthotic blank to be direct molded.

A posting material is used to post the bottom of the orthotic eliminating the need for grinding the base of the orthotic. The posting material has a molding temperature in the range of 140-200 degrees Fahrenheit, and the posting material is spreadable to a thickness of 0.002 inches at the molding temperature. This allows very accurate molding of the posting layer without requiring grinding. An example of such a posting material is known by the name Rebound from Chesapeake Medical Products, Inc, Baltimore, Md. 21237, and is often used for direct molding of hand splints.

Combining the design and materials noted above enables a technician to build a custom orthotic in minutes, usually 20, instead of hours with minimal training.

There are various components used in the different layers of the orthotic of the present invention. The first layer, closest to the foot, is called the top cover and is made from leather, vinyl or cushioned material like EVA (Ethylene Vinyl Acetate), Silicone or rubber to name a few. The top cover can be 0.5 mm to 6 mm thick depending on the shoe and/or sport the orthotic is being used for.

The second layer is the shell layer. This layer can be made of plastic, carbon fiber, fiberglass or other plastic or heat moldable firm rubber like EVA or similar materials. The shell is the core of the orthotic and the component which everything else is made around it. Shells are generally 0.5 mm to 6 mm thick.

The next layer is the posting layer. This reinforces the orthotic, filling the voids under the foot. It can extend from the heel to the ball of the foot. This layer preventing the foot's arch from collapsing and acts as the stabilizer, creating a wide flat area under the heel to prevent the orthotic from rocking.

The shape of the orthotic of the present invention, and the combination of its plastic layers is an important feature of this orthotic system. The shell is made of a low temperature thermoplastic used in heel counters and toe boxes of shoes. The low molding temperature of the material allows for direct molding to the foot without causing discomfort or burn injuries. The thermoplastic is heat moldable at 140 to 200 degrees Fahrenheit.

The shell layer has two layers of woven polyester fibers ("scrim") on the top and bottom. The scrim gives the plastic strength and prevents it from stretching excessively when molding. These unique properties make the material well suited for stacking multiple layers/sheets without having excessive bulking of material top lines.

Both sides of the shell layer, or each individual shell sheet are coated with a layer of hot melt cement/glue/adhesive for easy attachment of various layers or other materials. The orthotic unit of one embodiment of the present invention is composed of three shell sheets and a top cover layer/sheet for four sheets/layers in all, but the orthotic can be made of any number of shell sheets.

Another part of the present invention is the shape of the unmolded flat orthotic blank. The shape of the unmolded orthotic blank creates a molded orthotic with top clean edges, straight sides and a symmetrical round heel cup that don't require trimming or grinding.

Existing orthotic blanks with straight lateral side and symmetrical round heels look nice when flat and unmolded but yield uneven, wavy edges and lines when molded. This isn't desirable for both esthetic and functional reasons. It not only makes the orthotic look odd, but the foot's heel will not sit properly in the orthotic heel cup resulting in pressure spots and will need an experienced technician to correct the problem with a grinder.

In the present invention, the orthotic blank's shape creates an orthotic that can require no grinding. Unlike other orthotics, when unmolded the orthotic blank has no straight lines or boarders. The lateral side of the blank is not straight and instead is pocked or concave between the widest part of the outside of the heel and the widest part of the outside of the forefoot by the base of the fifth toe. But when the orthotic blank of the present invention is heated and molded, the lateral sides are straight and not wavy like those orthotic blanks that are designed with straight lateral edge and round heel shapes.

In this new design, the flat unmolded orthotic blank heel is not round and symmetrical. Instead it's slightly off-shaped. When heated and molded, however, the heel cup is perfectly round and symmetrical. With a round heel cup and straight lateral and medial flanges, the resulting orthotic requires no grinding to create flat even smooth trim lines. A technician needs only use scissors to match the toe shape of the footwear that it is going to be used in. Minimal experience needed for training. It can take as little as 20 minutes of training to make a professional looking device.

The heel, as well as the rear one-third of the lateral side of the foot, has curves and contouring that needs extra material to be able to adequately cup or cradle these areas. The orthotic blank needs extra material to be able to contour to these radiuses so it's able to wrap up around the foot. The extra material ensures the orthotic blank will wrap around these radii so there are no wavy trim/edge lines.

The shape of the orthotic blank of the present invention makes it easy to mold orthotic material. The outside of the orthotic blank is curved inward or concave with the apex of the curve being 1-4 mm deep. The smallest size has a shallow curve and which gets deeper in larger sizes.

The apex of the lateral curved arc is found by drawing a line from the widest part of the outside lateral aspect of the heel and the widest part of the lateral side of the forefoot. The widest part of the forefoot is ½-inch to 1-inch behind the fifth toe depending on the foot size. The center of the concave peak is 40% in from the back of the heel along this line. The odd, off-shaped heel curve and convex edges in the unmolded orthotic blank is what yields flat, smooth top edges when the blank is molded.

Another feature of the present invention is the way the shell layers react when stacked in multiple layers. This also holds true when using other shoe counter material that have both sides coated with hotmelt adhesive and layer of scrim on the top and bottom. When the material is warmed to 140 to 200 degrees Fahrenheit, it becomes soft and the layers will auto adhere due to the layer of hot melt glue that is coated on both sides.

When the shell layer or sheets are warmed to molding temperature, the scrim prevents the layer/sheets from stretching. The warmed hot melt allows the layer/sheets to slide or move over each other but lock together when cooled. When molding multiple shell sheets over a curved surface like the heel and lateral side of the foot, the material self bevels, especially at the edges. When the shell layer/sheets wrap around a curved surface of the foot, the first shell sheet will seem longer, extend further, than a second shell sheet due to the increase radius the second sheet has to wrap around the first sheet. A third shell sheet too seems shorter than the second sheet as it wraps around the second sheet and so on. Plastic materials without the scrim doesn't react this way because the material either will not bond or as they bond, will leave a thick top edge ridge that will need to be ground down.

When molding plastic without scrim, plastic with just one layer of scrim, or multiple layers of plastic greater than 2 mm thick, an orthotic will have a sharp edge around the heel and lateral side of the foot. This edge will push into the heel causing pain. A technician can fix this with a grinder and years of training. The thick edge will create excessive bulk taking too much space in the shoe and making the shoe fit too tightly. Furthermore, this thick edge will create excessive pressure on the foot creating a blister or a pressure point and pain.

Another time consuming process that takes time and is difficult to master is posting. Posting is the process of filling in the bottom of the orthotic so the orthotic sits flat and doesn't move or rock side-to-side. Posting adds stability and reinforces the orthotic making it stronger and better able to support the body's weight. The previous process of posting requires glue (which gives off toxic fumes), expensive grinding and dust collecting equipment and years of training to learn the techniques of grinding the excess posting material flat. Posting is the hardest part of the orthotic process to learn and master and is more art than science.

The present invention has features to provide no-grind, no-glue posting of the orthotic with minimal technician training. Heel posting is accomplished by using a thermoplastic posting material that is self adhesive to the shell layer and spreadable to a thickness of at least 0.002 inches at the molding temperature, preferably 140-200 degrees Fahrenheit. One such material is know as Rebound from Chesapeake Medical Co. There are other materials that can be used for the posting material, such as Aquaplast and other plastics containing polycaprolatone, $(C_6H_{10}O_2)_n$. These material mold at a low temperature, 140-160 degrees F. Rebound is beneficial because of its low temp moldability and better draping characteristics compared to similar plastics and the fact that it is available in colors.

Other low temperature thermoplastic that would work for the posting aspects are: Rolyan Aquaplast, Orfilight, Rolyan Sandsplint, Rolyan Kay-Splint, Rolyan Orthoplast, Rolyan Ezeform, Rolyan Polyform, Rolyan Polyflex and Rolyan Synergy from Patterson Medical. From Chesapeake Medical Products, Inc. you have Excel, Infinity, FiberForm Soft, Rebound, Colours, FiberForm Stiff and Marque-Easy. And from Smith & Nephew—Australia, you have Dynacast # Prelude.

The posting material becomes very soft at 140-160 degrees Fahrenheit and at this temperature it is auto-adhesive and will adhere to itself or the shell layer without the use of any glue or other adhesive. The posting material is preferably used in 1/16", 1/12", 1/10" and 1/8" thickness in both perforated and solid sheets. 1/10" solid material is especially preferred for use in the present invention. When warm, the posting material drapes and molds with little pressure. In fact with as little as 15-20 lbs. of pressure the posting material will compress flat or paper thin. At 140 degrees the posting material is so soft it flows to areas that are under little or no pressure.

Grind-less posting can be accomplished by using this posting material. This plastic posting material works and function much like polyethylene or polyurethane. The difference between this posting material and most other plastic is the molding temperature: 350 degrees Fahrenheit for the poly-type plastics and the 140 degrees Fahrenheit for molding the posting material of the present invention.

Unlike the thermoplastic material of the shell layer, the material of the posting layer has no fibers to reinforce the plastic, and at 140-160 degrees F. the material of the posting layer drapes and wraps around contours easily.

The present invention makes the orthotic/orthosis by a method that will be called Direct Molding. When making an orthotic using plaster wraps or impression foam you need to pour plaster inside the mold to create the positive impression of the bottom of the foot. Direct Molding methods eliminates the plaster molding process. With Direct Molding the foot is used as the "mold" and a casting tray filled with moldable material such as foam pillows hold the orthotic blank snug around the bottom of the foot. The individual places the foot, or other body part, with the heated orthotic blank into the casting tray and against the foam pillows. The foot and the foam pillows press against each other and force the heated orthotic blank to mold around the foot.

Both the posting material and the shell material have the same molding temperatures and heating times are the same for similar thicknesses of both materials. Both materials can be heated in identical manner including immersion in boiling water, use of a convection oven, heat lamps, microwave oven, heat gun, heated plate press, or a thermal roller heating system often used for laminating materials in a plastic covering such as those used for license. The thermal roller heating system is the preferred method of the present invention in several embodiments such as an insole for walking shoes and ski boots because of its speed and ease. The roller heating system, is optimal for heating both the shell and post materials. The thermal rollers create a sheen on the EVA top cover which makes it slippery. The sheen works well in ski boots because the slick surface makes it easier to slide the foot in and out of tight ski boots. When the boot is buckled snug around the foot the foot can't slide or move. For walking the sheen prevents blisters as the foot slides instead of rubbing on the top cover. The heated plate press, which operates similar to the familiar Panini press, works best for cycling because the top cover maintains its grip so while pushing up and down on the pedals the foot doesn't slide which could cause blisters and loose pedal power.

Until now a thermal roller heating system has not be use for heating orthotic blanks. The thermal roller heating system is one of the fastest methods for heating the orthotic blank to the proper molding temperature. In addition the rollers are spring loaded or biased toward each other. When the blank is put through the machine, the rollers lock the warmed layers together while the pressure of the springs compresses. This also bevels the edges and pushes the posting layer into the shell layer firmly adhering them together. The thermal roller system heats a small blank to optimal molding temperature of 140 degrees F. in as little as 50 seconds. Larger orthotic blanks heat in less than two minutes.

The orthotic blanks are put through the thermal roller system in a paper release liner folder coated with silicone or Teflon to prevent the hot shell layer/sheet material from sticking to the rollers. The release liner is preferably a 13"×8" sheet that is folded in half to create a 13"×4" folder.

The blank is inserted into the release liner folder and then inserted into the thermal roller system toes first so the heel emerges last. It is inserted toe first to maximize heat retention in the heel for better wrapping and draping ability around the foot heel. If the orthotic blank is not hot enough it will not mold precisely around the heel.

Because both the shell layer material and the posting material are very sticky and auto adhesive when hot, there is no need for glue, but a release liner must be used when heating. When heating the shell layer thermoplastic material by any means other than the laminator, such as boiling water, oven, microwave oven or heat gun, the orthotic of the present invention should be placed with the cover layer down to prevent the thermoplastic material of the shell layer from sticking to the supporting surface.

If the orthotic blank is heated with the cover layer side up, it will cause the cover layer to shrink. The posting material, regardless of heating method, also needs a release liner to prevent it from sticking to the oven or laminator. Paper release liner coated with silicone and Teflon sheet work best for preventing the material from sticking to surfaces. Paper silicone release liner works well for both the shell layer material and the posting material. Heating the posting material using a combination of a Teflon sheet and silicon paper gives the post a textured look while making it easier to handle when hot and prevent it from sticking to the working surface.

Depending on the type of materials used for the shell layer and the posting layer, the thermoplastic of one layer or the other layer, or both may need to be treated so that the materials of each layer will adhere to each other. The thermoplastic materials of the different layers can be treated with acetone, paint thinner, alcohol and/or other solvents and thinners to get the material of the posting layer to adhere to the material of the shell layer. Xylol, also known as Xilene, works well for treating the material of the shell layer and only the side of the shell layer in contact with the posting layer needs to be treated. The shell layer and posting layer can also be flash cooled to lock the two layers together.

A orthotic blank of the present invention can be repeatedly reheated without any loss of material strength or integrity. A molded orthotic blank can't be reheated in the roller heat system unless the orthotic blank is first reheated in an conventional oven, convection oven, by heat gun or hot water and then flattened. At this point the warm orthotic blank can be remolded using the Direct Molding technique or cooled for use at another time. A used, flat, cooled orthotic blank can be reinserted into the roller heat system at anytime.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a schematic cross sectional view of the shell layer of one embodiment;

FIG. 4 is a schematic cross sectional view of the shell layer in another embodiment;

FIG. 6 is a bottom view of the flat unmolded blank;

FIG. 7 is a cross sectional view of the molded blank;

FIG. 8 is a rear view of the molded blank;

FIG. 9 is a perspective view of the molded blank;

FIG. 10 is a view of the posting layer wrapped in a liner;

DESCRIPTION OF THE PREFERRED EMBODIMENTS

Figure 1:
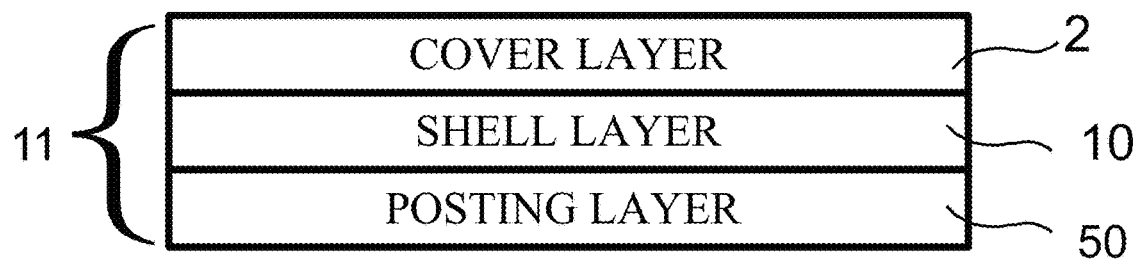
FIG. 1 is a schematic cross sectional view of one embodiment of the orthotic blank.
Figure 2:
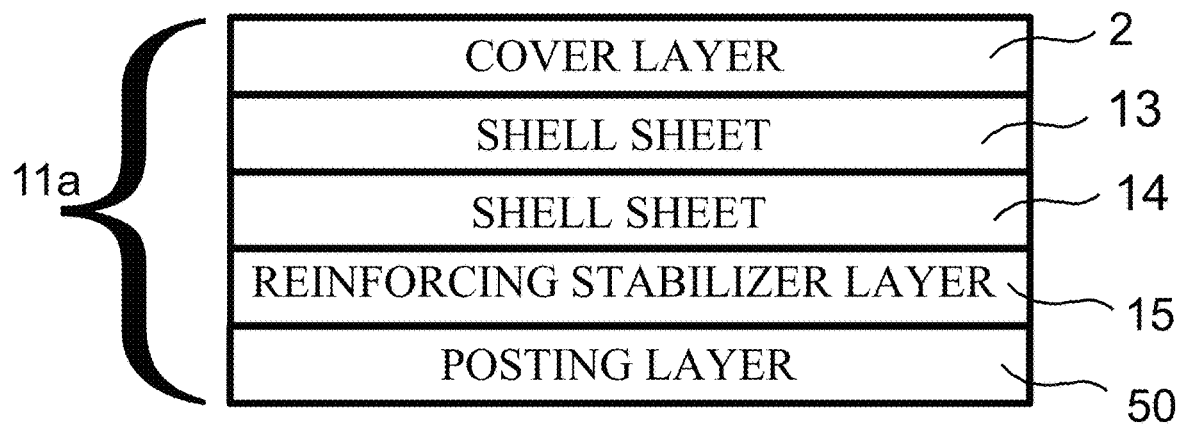
FIG. 2 is a schematic cross sectional view of another embodiment of the orthotic blank.

Referring to the drawings in particular, the orthotic blank 11 shown in FIG. 1 includes a cover layer 2, a shell layer 10, and a posting layer 50. In another embodiment, such as shown in FIG. 2, the orthotic blank 11a includes a cover layer 2, a plurality of shell sheets 13, 14 forming the shell layer 10, a reinforcing stabilizer layer 15, and a posting layer 50.

FIG. 3 shows a schematic cross sectional view of one embodiment of a shell sheet 13. The shell sheet 13 has a center ply formed of a thermoplastic material 12 having a molding temperature in the range of 140-160° F. This thermoplastic material 12 preferably includes polycaprolactone $(C_6H_{10}O_2)_n$ and a plurality of fibers to reinforce the thermoplastic material 12. On either side of the thermoplastic ply 12, on diametrically opposite sides, there is a scrim ply 31. On each side of the scrim ply 31 diametrically opposite the thermoplastic 12 is a hot melt adhesive/cement ply 8.

It is also possible for each side of the hot melt adhesive/cement ply 8 diametrically opposite the thermoplastic 12 to have a scrim ply 31. This scrim ply 31 can be formed from woven polyester fibers, or other material, to give the shell sheets 13, 14 strength, and to prevent the shell sheets from stretching excessively when the blank 11 is heated up to the molding temperature and molded around the body part. The scrim ply 31 can also be embedded in the hot melt adhesive/cement ply 8 or in the thermoplastic 12. The scrim plies preferably include a plurality of strands woven like a screen forming 2 mm to 4 mm grid areas.

Figure 5:
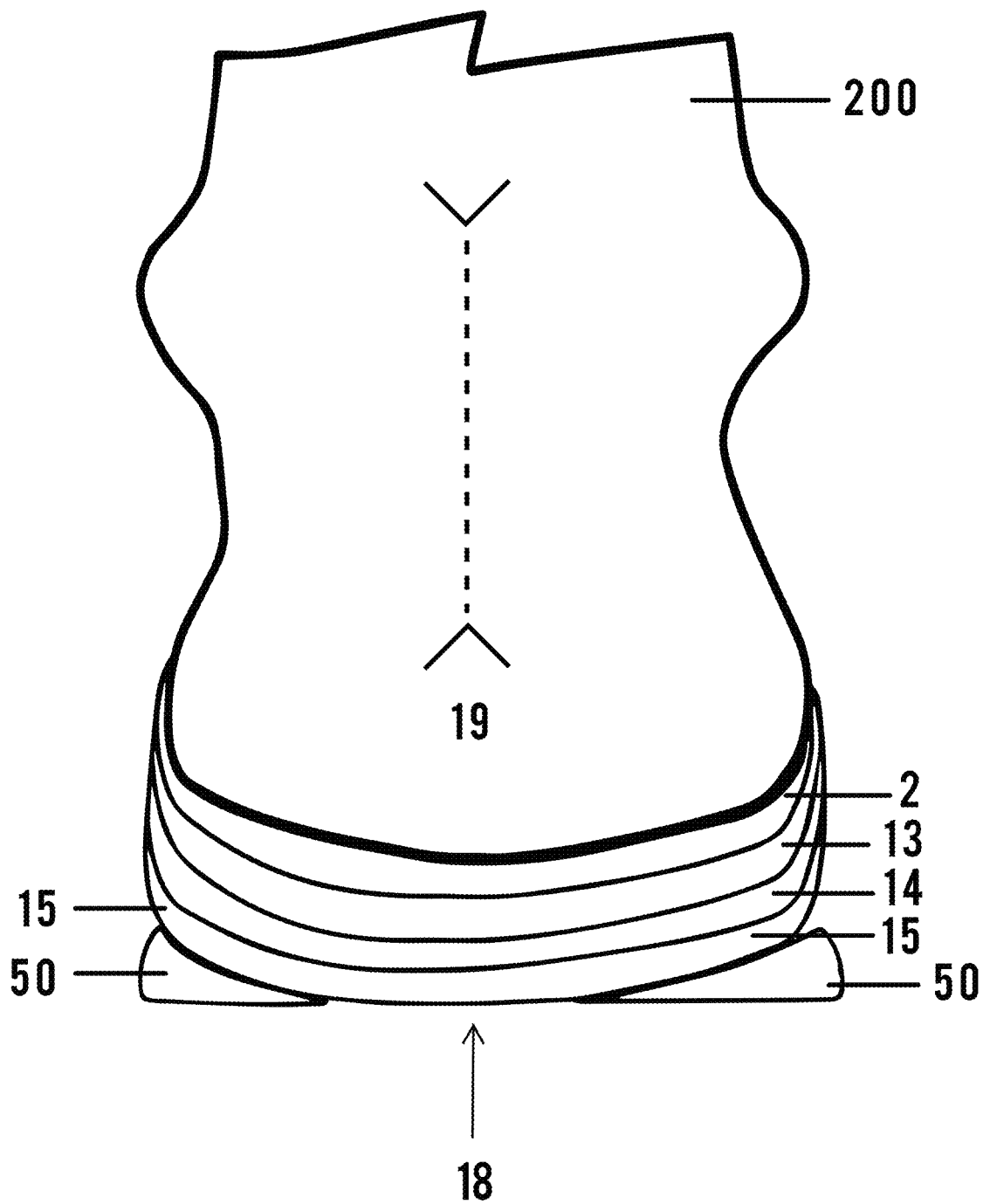
FIG. 5 is a schematic cross sectional view of one embodiment of the orthotic blank in contact with a foot of an individual using the orthotic/orthosis.

If the body part is a foot, the blank 11 is molded around areas such as the medial side of the heel 17, the back of the heel 19, the lateral heel side 20 and the lateral flange 25, as shown in FIGS. 5-7. Each shell sheet 13, 14 is preferably 1.2 mm thick and stacked together to yield the best combination of flex and rigidity.

A reinforcing stabilizing layer 15 can added between the shell layer 10 and the posting layer 50. This reinforcing stabilizing layer 15 can be formed of the same material as the shell sheets 13, 14, and preferably has a cutout 118 that receives an apex of the curve caused as the other shell sheets 13, 14 wrap around the body part, preferably the foot.

Examples of composites that can be used for the shell sheets 13, 14 are available under the name Proform manufactured in Spain by the Texon Company, and Wonderflex by The Jeffrey Nonwovens Group, LLC.

The shape of the orthotic 11 and its layers is important in making a truly grind-free orthotic. Each layer is slightly smaller than the next layer. Each layer is 5 mm or 5-7% narrower than the next layer 12, 13, 14 and 15. The top cover layer 2 of the orthotic 11 can be made from leather, vinyl or cushioned material like EVA (Ethylene Vinyl Acetate), Silicone or rubber which acts as a shock absorber and a cover for the orthotic 11. The topmost shell sheet 13 in a multi-shell sheet embodiment is preferably made from a single layer that is 1.2 mm thick. This sheet 13 can be full length or it can be made three-quarter length. The next shell sheet 14 is a shell reinforcement and is also preferably made from a single layer that is 1.2 mm thick. This shell sheet 14 is made to a three-quarter length of the foot. The last shell sheet is the reinforcing stabilizing layer 15 with the oval cut out, and there are 6 sizes xs, s, m, l, xl, xxl. The smallest oval is for the xs sizes, and the oval gets larger by 3 mm wider and longer as the size goes up. For the smallest size the preferred width and length is 12 mm×16 mm but it can be 2 mm plus or minus.

In regards to the posting layer 50 there are 3 sizes s, m and large. The posting layer 50 accommodates 2 sizes per shell reinforcing stabilizing layer 15. The posting layer 50 cutouts are large 4-6 mm larger in length and width than the shell reinforcing stabilizing layer 15 cutout. The large oval cutout in the posting layer 50 allows for the posting material to flow under the heel when heated to cradle the base of the heel giving it a wider base of support stabilizing the insole/orthotic preventing it from rocking or collapsing.

The posting layer 50 adds strength and stability to the orthotic. The posting layer is formed of a posting material having a molding temperature in the range of 140-200 degrees Fahrenheit. The posting material being spreadable to a thickness of 0.002 inches at the molding temperature. The posting layer 50 also has a cutout 18, preferably oval, under the center of the heel to reduce bulk and add stability by giving the heel a broader base. This allows the posting material to become very thin in the area of the cutout 18. At the molding temperature the posting material flows under pressure and the edges under the heel any area of the cutout become paper thin. The posting material can be considered to be self beveling and thus produces a smooth bottom without needing to grind excess material. Some materials because of various properties cannot be spread thin enough and if used for the posting layer, those materials will result in excessive bulk under the heel which requires grinding to remove the excess bulk. The posting material should therefore be soft and very pliable in order to spread very thin at the molding temperatures. Below the molding temperatures is preferable that the posting material is harder and denser than the thermoplastic 12 of the shell layer 10. The posting material is preferably also more elastic, and should better return to its original shape when deformed (elastic memory), than the thermoplastic 12 of the shell layer 10. The tear strength of the posting material should also be greater than the thermoplastic 12 of the shell layer 10. The posting material should have properties similar to polypropylene when cool, and yet be moldable in a temperature range of 140-200° F.

The reinforcing stabilizing layer 15 if used, also adds strength and stability to the orthotic. The cutout 118 of the reinforcing stabilizing layer 15 is smaller than the cutout 18 of the posting layer 50. The cutouts 118 and 18 under the center of the heel reduce bulk and add stability by giving the heel a broader base.

The 1.2 mm thickness of the layers is the preferred thickness when making arch supports. The orthotic blank 11 can be a four layer/sheet design 2, 13, 14, and 50, but can be three layers for a smaller person. The fifth layer 15 can be used to add extra stability and balance the heel. Depending on the activity and the weight of the person the layers/sheets are assembled differently. For example, for skiing and bicycling the orthotic's 11 cover layer 2 can be 2 mm thick while for walking and running and court sports the top cover can be 3 mm thick. The next three layers/sheets can be the layers/sheets 13, 14, and 15.

The shell sheets can also be formed by two full length sheets, or it can use one full length sheet 13 and one three-quarter sheet 14 for an orthotic 11 that would take less space in the footwear. This construction is used for the wider foot or a different activity.

Figure 15:
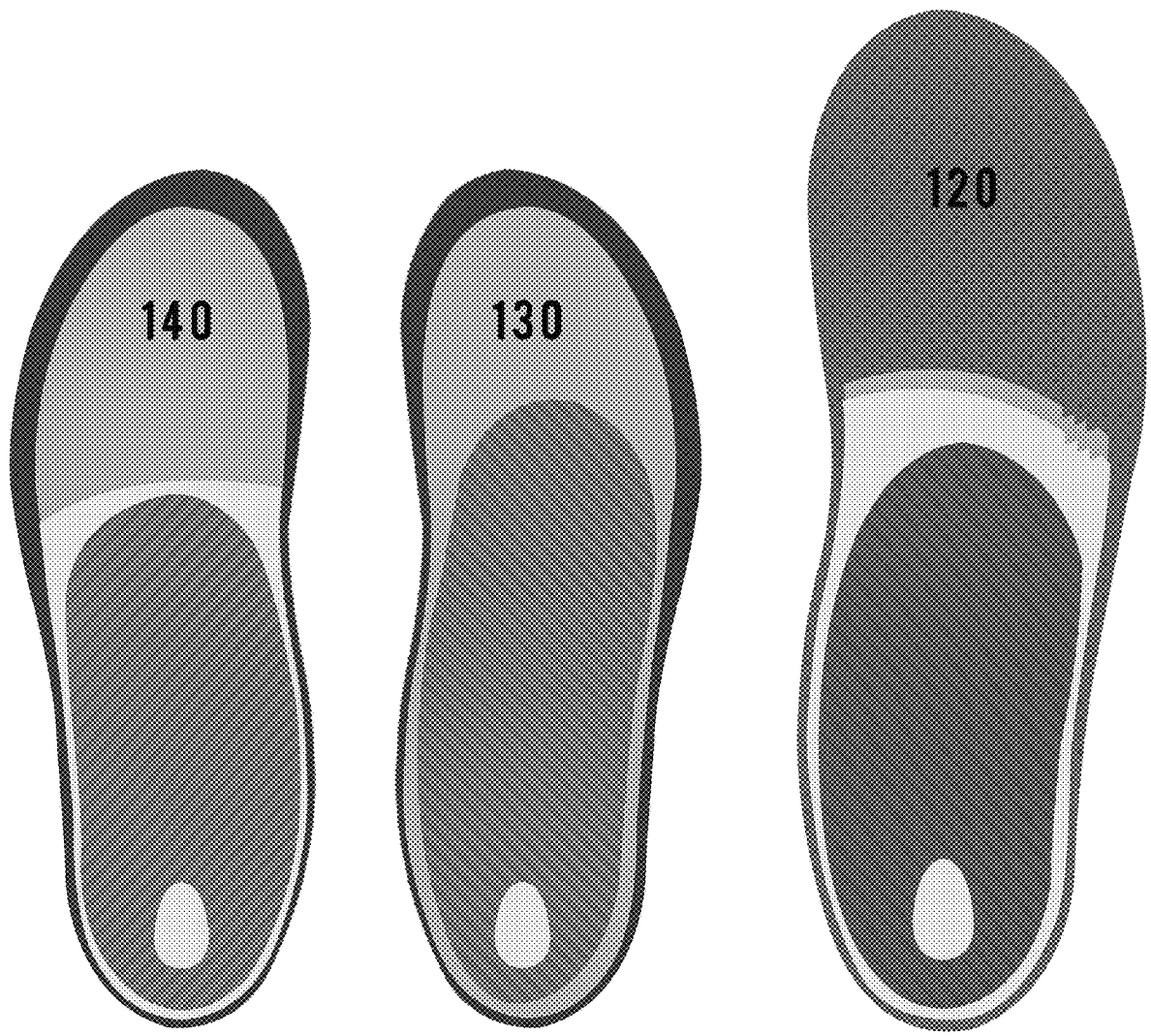
FIG. 15 is a bottom view of three different embodiments of the present invention.

When using multiple sheets/layers 13, 14, 15 of ¾ length, the front edges 23 have to be 5 mm to 7 mm shorter to prevent a thick edge or step from forming, an example shown in FIG. 15 by insole 120. By having each layer/sheet's front edge 23 slightly shorter, the material self-bevels preventing a thick edge or step that would feel uncomfortable. When stacking shell layers/sheets 13, 14 15, the material's front edge 23 has to be shorter than the next layer/sheet. However, the width does not have to end shorter due to the scrim 31, and that both sides are coated with a hot melt cement, this allows the shell layer/sheets 13, 14, and 15 to side or move over each other.

When molding multiple layers/sheets over a curved surface, such as the medial side of the heel 17, the back of the heel 19, the lateral heel side 20, and the lateral flange 25, the scrim 31 prevents the layers/sheets 13, 14, 15 from stretching as it wraps around a contoured surface, allowing each layer/sheet to end shorter than the next, and resulting in a self beveling of the orthotic top edge. As the cross sections in FIGS. 5 and 7 show, as the layers/sheets 13-15 wrap around the lateral side of the heel 20, the top shell sheet 13 wraps close around the foot 200. The second shell sheet 14, which has the same width as the first shell sheet 13, seems shorter due to the increase radius as it wrap around the first shell sheet 13. The same holds true for each of the additional layers/sheets.

When designing an orthotic its important to keep the orthotic thin. You don't want an orthotic that is thicker than the stock insole. With a thick orthotic, the foot loses feel for the ground and the footwear feels too snug. In the present orthotic 11, the reinforcing stabilizing layer 15 has an oval cutout 118 in the heel. The heel cut out 118 has two purposes. First, it keeps the foot 200 lower because of the 1.2 mm cutout, so there is less material, 1.2 mm, under the heel. Secondly, it creates a flat spot 26 stabilizing the orthotic 11 and giving the heel a wider more stable base around the center of the heel. This prevents the orthotic 11 from rocking. Looking at the cross section 24 in FIG. 7, the reinforcing stabilizing layer 15 has an oval cutout 118. This cutout 118 gets larger as the size of the orthotic increases, the oval increases 2 mm to 4 mm depending on the size of the orthotic blank. When the layers/sheets 13, 14 or 15 are warmed, they drape and wrap around the back of the heel 19, the lateral side of the heel 20, and the medial side of the heel 17. At the same time the weight of the foot pushes down on the orthotic 11 during the molding process. Because the heel is round or bulb-like in shape, the center of the heel pushes in and around the cutout 118 setting the heel into the posting layer 50.

The shape of the unmolded orthotic blank 11 is important. Most unmolded orthotic blanks have straight lateral edges 21. Whereas the present design has the outside of the orthotic blank 11 being curved inward or having a concave curve 30, FIGS. 5 and 11. The apex of the curve 30 is 1 mm to 4 mm deep depending on the size of blank 11; less for the smallest size and increasing as the orthotic size increases. The increase is 0.5 for smaller sizes to 1 mm for larger sizes. The apex of the curve 30 is found by drawing a line 21 from the widest part of the heel 20 and the widest part of the forefoot 22. These widest parts can also be where a straight line 21 would touch the blank 11 at only two points, or where the straight line 21 would first touch the heel and forefoot parts as the straight line was brought against the blank 11. Then measuring 40-50% down the straight line 21 from the heel to find the center of the apex. This curve shape insures a straight lateral flange 25 and heel cup top edges that are round and level when molded. Straight lateral boarders 21 in the unmolded orthotic yield non level, wavy lateral walls 27, FIG. 9, and form a downward curving rim on the heel cup top edges 28. This concave or recess forms a negative angle curve 30 on the orthotic blank 11 of 3 to 20 degrees.

Figure 11:
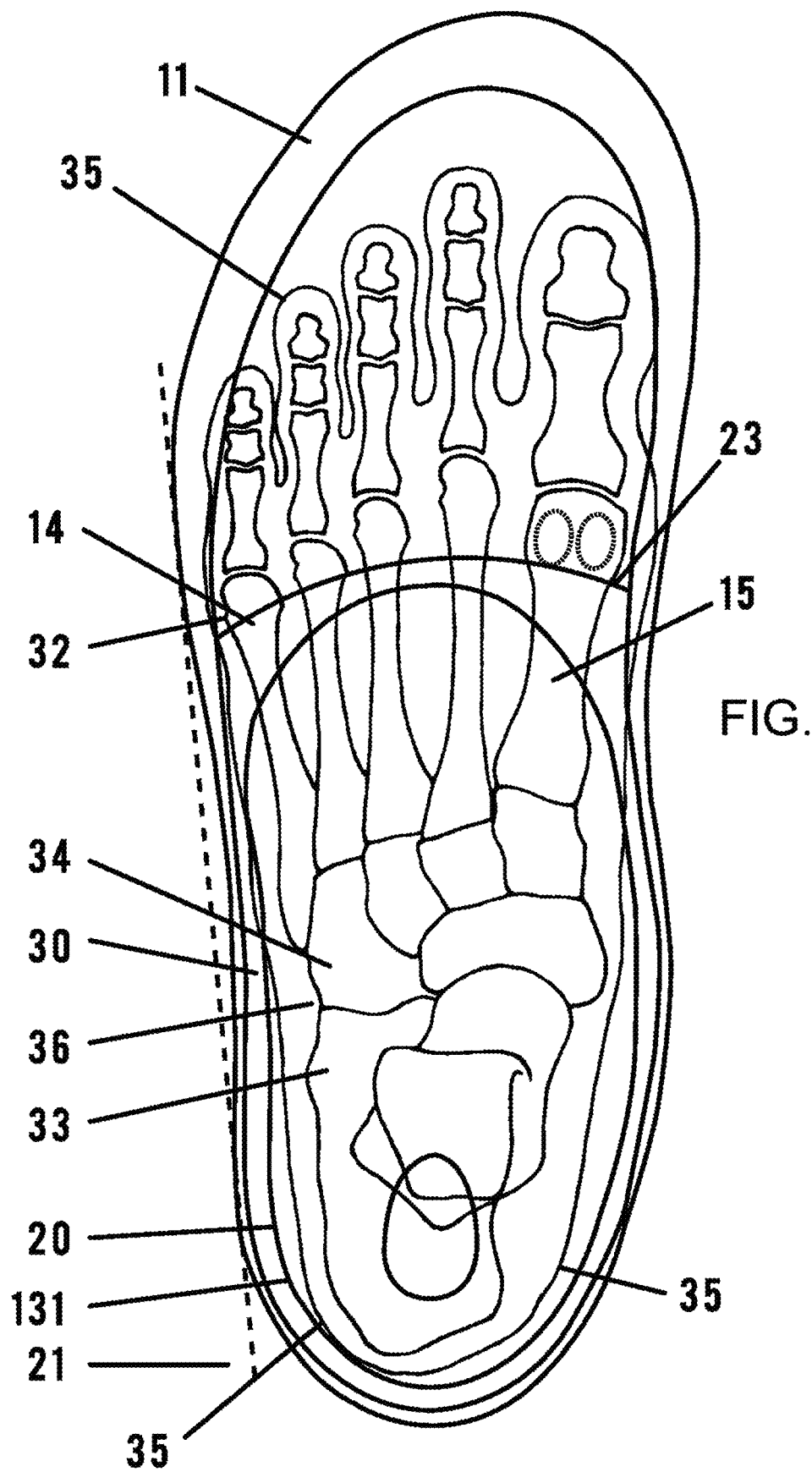
FIG. 11 is a bottom view of a foot superimposed on the insole.

When the bones and the outside border of the foot 35 are superimposed, one can see the apex of the curve 30 is between the calcaneus 33 and the cuboid bone 34, FIG. 11. The foot structure is narrower at this point or pocked 36. The widest, or furthest extending, part of the lateral side of the heel 20 is where the back of the heel radius 131 rounds out or ends, and the foots lateral border 20 straightens. The widest part, or furthest extending part, of the forefoot is the base of the fifth metatarsal 32. To find the apex of the recess, a measuring line 21 is extended, between the base of the fifth metatarsal 32 and the lateral border of the heel 131, and then divide by two to find the apex of the recess.

Figure 12:
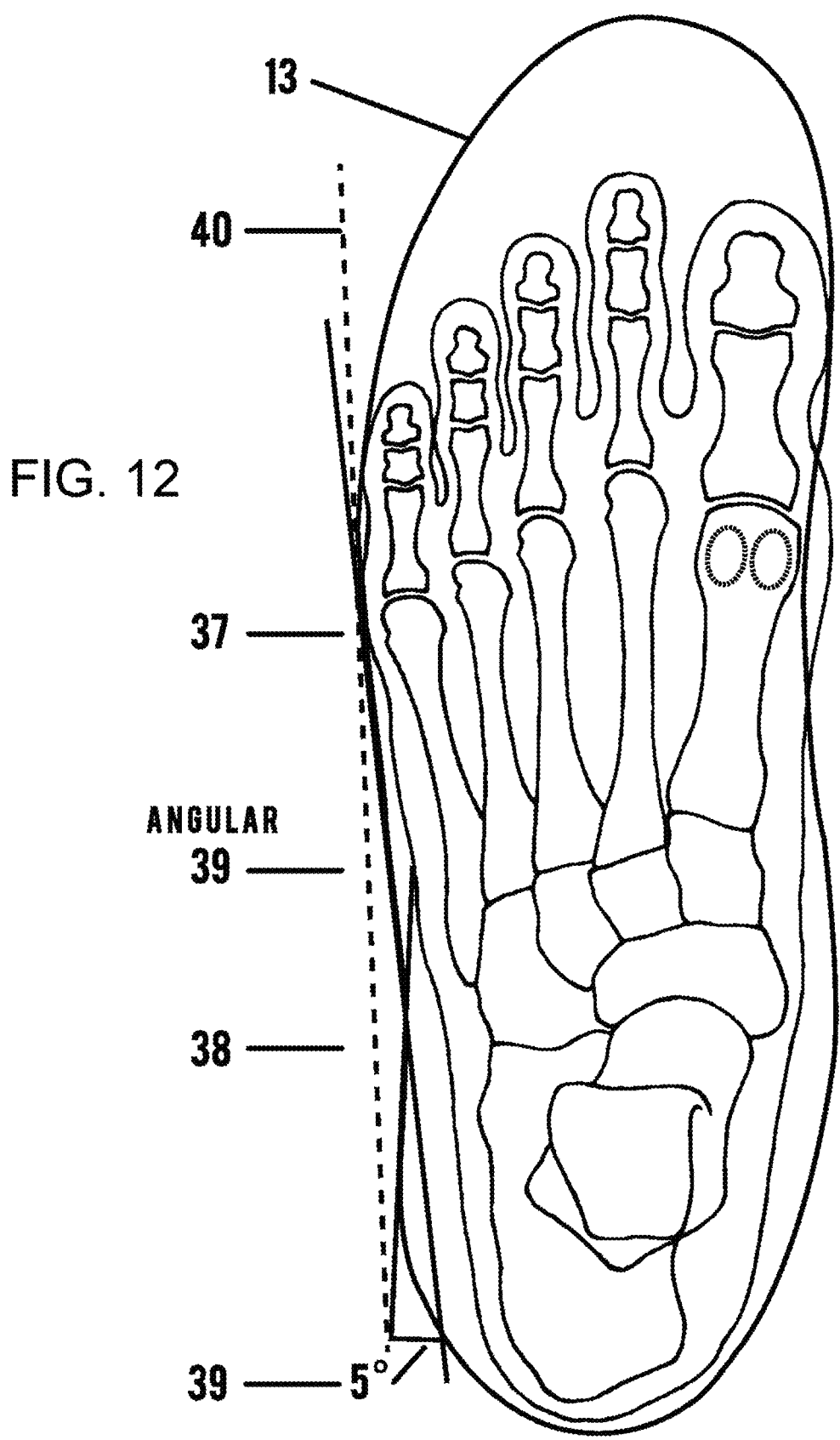
FIG. 12 is a top view of a foot superimposed on the insole.

In the present invention the top cover layer 2 has an oblique toe shape with the area behind the metatarsal heads 32 having the same shape as the cover layer 2 but having a 2.5 mm narrower border. The toe shape doesn't have to be oblique, and can have the same shapes as shell layer 13 but with the perimeter being 2.5 mm wider on each side. FIG. 12 shows this. Each additional sheet/layer 13, 14, and 15 circumference is smaller by 2.5 mm, or 5 mm narrower than the next layer. The negative angle is found by drawing a straight line from the widest part, or furthest extending part, of the forefoot 32 parallel foot border drawing a straight line 37 towards the heel. Then another line drawn 40 from the widest part 32 of the forefoot straight back at a vertical line 40 straight back to the heel. Then another line is drawn 38 from this point in line with widest base of the heel 131 half way in to fine the negative angle 39 which measure 3 to 5 degrees.

Figure 13:
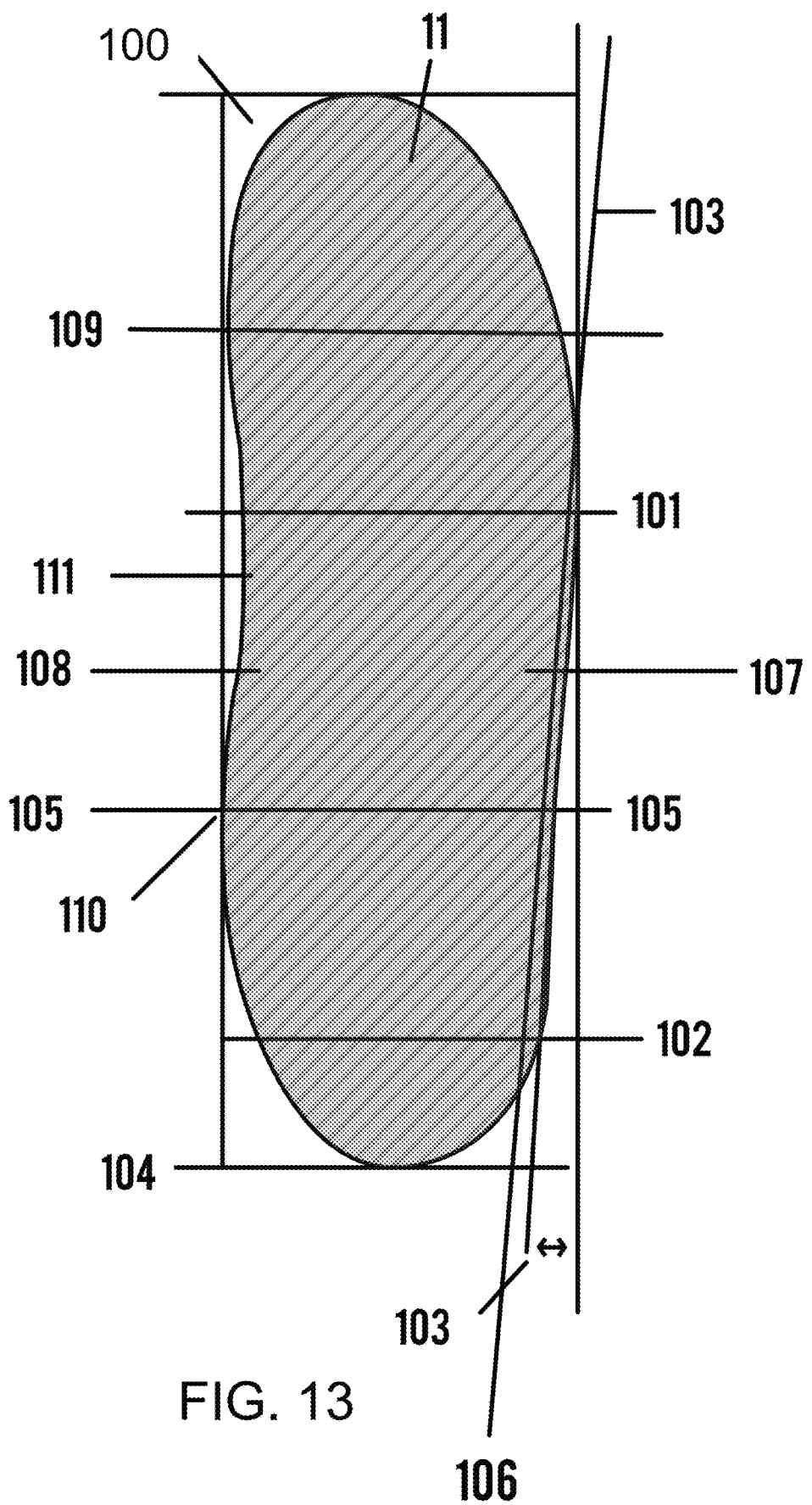
FIG. 13 is a top view of the insole surrounded by a hypothetical rectangle.

Another way to describe the curve is by using a rectangle 100 encompassing the insole 11 then marking the widest point 101 on the lateral side 107 of the insole 11, as shown in FIG. 13. Then marking the widest spot on the lateral side of the heel 102. The widest spot of the heel 102 is about 21 to 22% of the distance between points 104 at the rear of the insole 11 and the widest part 101 on the lateral side 107 of the insole 11.

Then if you draw a line from the widest spot 101 on the lateral side 107 and the widest spot 102 on the lateral 107 side of the heel this would form at 3 degrees to 4 degrees angle 103. Then if you measure the distance between the widest spot 102 on the heel and the widest spot on the lateral 107 side of the forefoot 101 then make another mark 44% to 45% in from the widest spot of the heel 105 this would be the narrowest 105 point on the lateral side 107 of the insole would be at the spot 105 the insole would have a recess. Then if you draw a line from the widest point 101 on the lateral side 107 of the insole 11 and the narrowest insole 105 this would form a 4.5 to 5.5 angle 106. This recess 105 would measure 2 mm to 4 mm in from the line 103.

Then on the medial side 108 of the insole 11 you measure the distance from the back 104 of the insole 11 to the widest point on the front of the insole 109 and then you measure in 42% to 43% to find the wide point on the arch 110. The widest point on the arch 110 is at the same point where you find the narrowest point 105 of the lateral side 107 of the insole 11. Then to find the narrowest 111 part on the medial side 108 you measure the distance between the back of the heel 104 to the widest point 109 of the medial side 108 and make a mark 79 to 80 degrees to find the narrowest point 111 on the medial side of the insole 11. This narrowest point 111 on the front of the insole is 3 mm to 9 mm in depending on the size of the insole 11.

Figure 14:
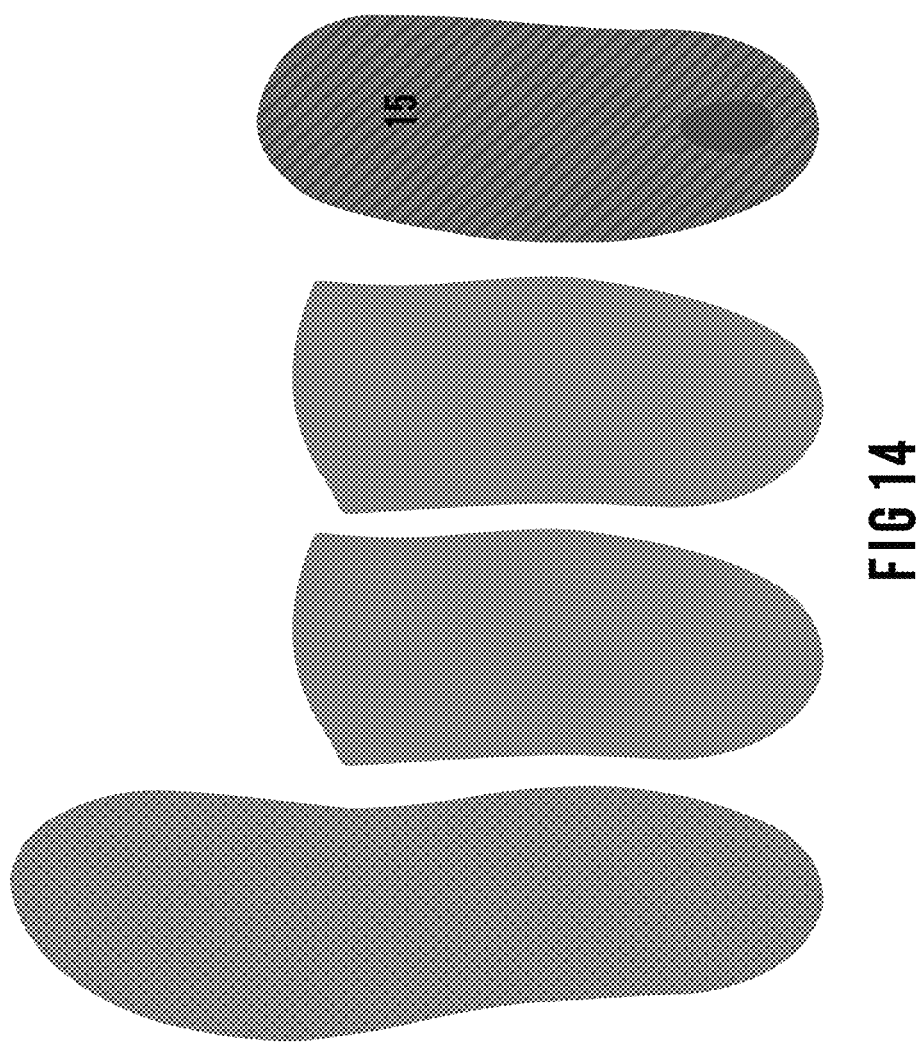
FIG. 14 is a top view of the different layers of the insole.
Figure 16:
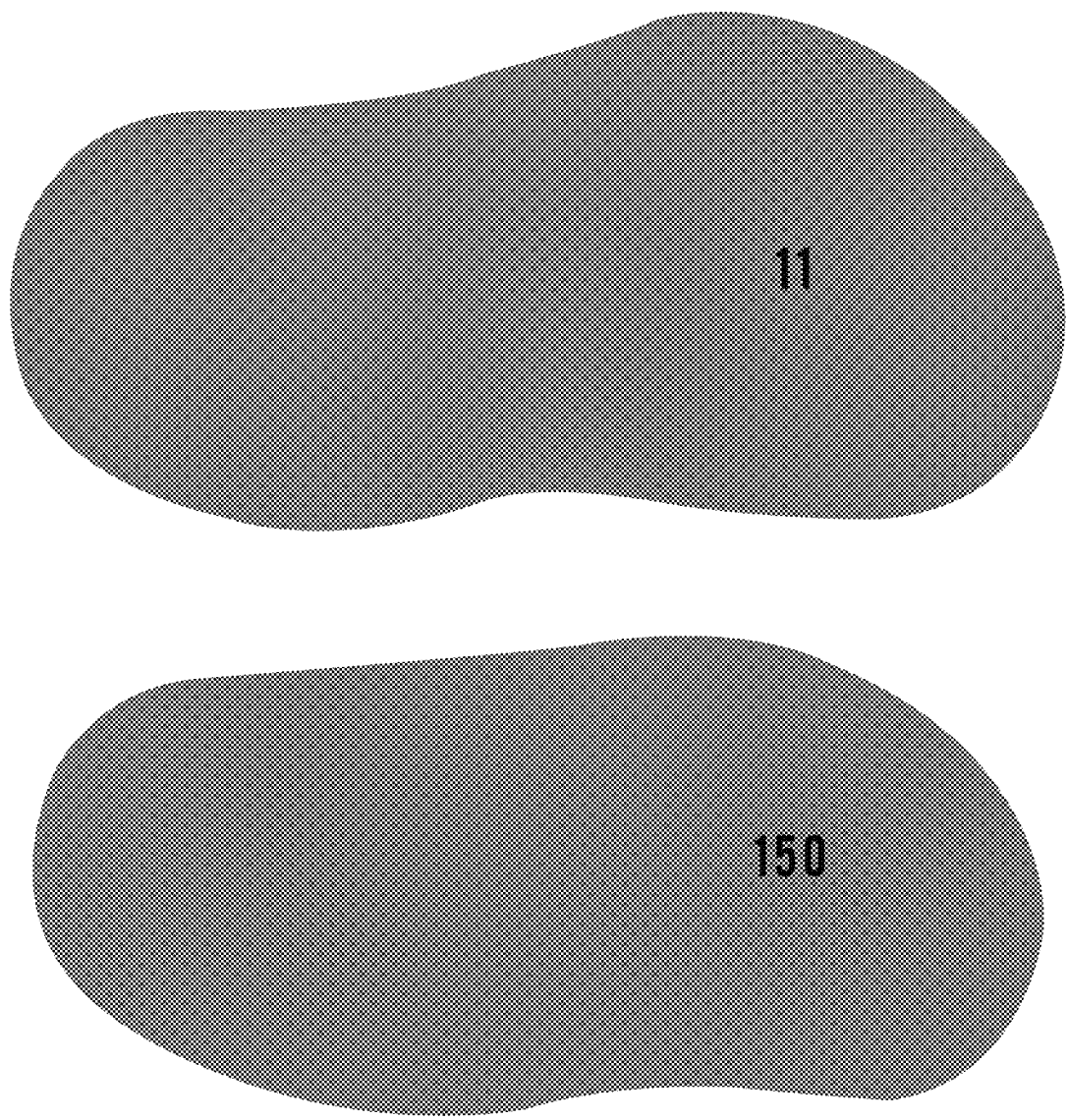
FIG. 16 is a top view comparison between an insole of the present invention and the prior art.
Figure 17:
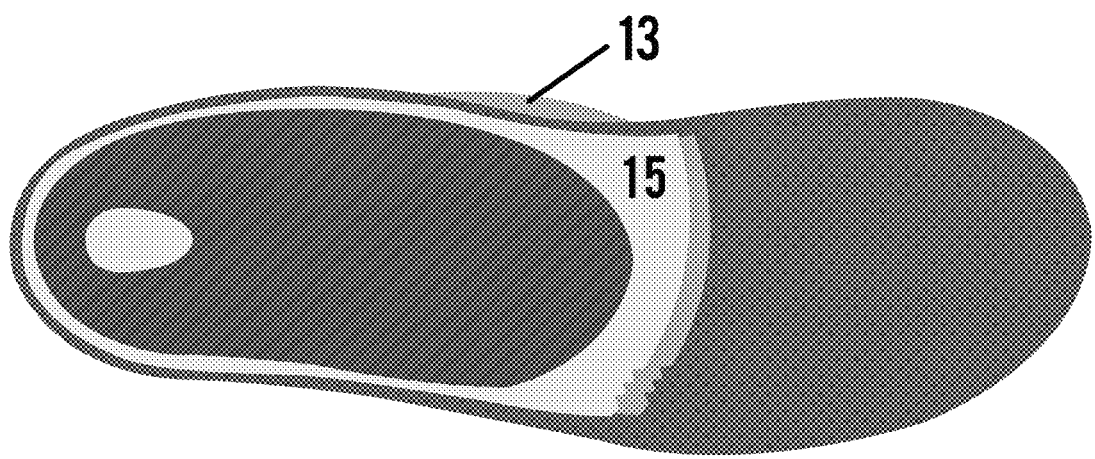
FIG. 17 is a bottom view of the insole of the present invention showing the different layers.

The different layers 2, 13-15 can have different widths, lengths and shapes as shown in FIG. 14 which shows the four components that are used to build the various orthotics (insoles). Cover layer 2 is not included in FIG. 14. FIG. 15 is a view of three different models of the insole. A walking insole 120 is the model on the right, a ski insole 130 is shown in the middle and a bike insole 140 is the model to the left. FIG. 16 is a top view which shows the shapes of the insole 11 and of a prior art insole 150. The prior art insole 150 is wider and has a straight lateral border. The prior art insole 150 requires a lot of expertise to grind the insole after molding to create a proper insole. FIG. 17 show the bottom of the insole 11 of FIG. 16 with the unmolded blanks placed on top of each other, you will notice the tan color of the large blank 13 shows through while the top blank 15 is narrower on the lateral side and the medial side by the arch. These are the areas that would need to be ground down on the prior art blank 150.

Referring to FIG. 14, the first piece on the left is a full length shell that is used in the bike and ski insoles. The bike insole uses only one of these layers while the ski model uses two of these layers. The second piece is ¾ shell that is use with bike insole and walking models. It's narrower than the first layer. This layer is also use for the walking insole and is the first layer. The third piece is shorter that the second piece and is used only for the walking insole. The reinforcing stabilizing layer 15 with the oval cutout stabilizes the whole insole system.

FIG. 15 shows the three different models, the walking insole 120 on the far right, the ski insole 130 and the bike insole 140. They all have a four layer/sheet construction if you include the top cover 2. The walking insole 120 uses three shorter pieces while the ski insole 130 uses two full length layers/sheets and the post, and the bike insole 140 uses one full length shell sheet, one ¾ shell sheet and the reinforcing stabilizing layer 15. They all use the same shape top cover layer 2. The layers in width and in length are slightly narrower that the next layer which creates a self beveled edges which don't require any grinding.

Once the shell layers/sheets 13-15 are formed to their proper shape, the shell layers/sheets are stacked on top of each other and heated. The stack of layers/sheets 13-15 can be heated using a thermal roller system. The flat orthotic blank 11 with layers/sheets 2, 13-15 are placed into a paper release liner folder preferably 13" long×4" wide with the cover layer 2 on the bottom. The cover layer 2 is placed down because of the graduation or pyramid structure of the layers/sheets 2, 13-15, which is wider on the top and thins as it goes higher. When the blank goes through the thermal roller machine it locks the warmed layers together while the pressure of the roller springs compresses and bevels the edges and pushes the layers 2, 13-15 into each other firmly adhering them together.

The blank 11 is inserted into the release liner folder, and then inserted into the thermal roller system toes first, so the heel emerges last. It is inserted toe first to maximize heat retention in the heel for better wrapping and draping ability around the foot heel. If the orthotic blank is not at the proper temperature it will not mold precisely around the heel.

At this point the orthotic is ready for molding around the body part using various systems. A semi-weight bearing casting system is preferred, and uses a preformed bladder filled with a proprietary blend or mixture of waxes, oils, and filler to cast the foot. There are casting modules or casting chambers for casting the foot and molding the blanks. The warmed blank is inserted into the casting module and the body part placed on top. The body part is pushed into the warmed blank and into the preformed bladder in the casting module. After five minutes, the material of the blank 11 has cooled. The foot and molded orthotic shell is then removed.

After the molded orthotic 29 is formed, the bottom needs to be balanced and stabilized to prevent the molded orthotic from rocking and/or collapsing under body weight. This is accomplished by a process called posting. The present design calls for a posting layer 50 to act as the post. An oval, square, round, heart shape, rectangle or similar shape piece of material is a fixed to the bottom 55 of the molded orthotic. The present invention, as shown in FIG. 10, uses a tear drop shape posting layer 50. The posting layer shape can be virtually any shape, even star shaped. The posting layer can be heated in an oven, by a heat gun, in a hot water bath or by a roller heat machine. The roller heat machine has been found to work the fastest and best to heat up the posting layer 50.

Warmed posting layer 50 is very sticky. A release liner, as shown in FIG. 10, is needed to prevent the post material from sticking to the working surface when heating. A combination of silicone paper and Teflon 52, 53 works well for heating and applying warmed posting layer 50 to a formed orthotic blank bottom 55.

After the orthotic is formed and cooled, it is ready to be posted using the posting layer 50. A single piece of paper silicone release liner 8"×4" rectangle is folded in half creating a release liner folder that is 4"×4" square, as shown in FIG. 10. The release liner folder is opened, a piece of posting layer 50 material is inserted on top of a 4"×4" square of Teflon 52,53 with both side edges 54 of the Teflon overlapping on top of the posting layer 50. The Teflon 52,53 is used to remove the posting layer 50 from the paper release liner and as an aid to laying and adhering posting layer 50 to the molded orthotic blank heel bottom 55. The Teflon will be used as an aid to laying the posting layer 50 on the orthotics heel 55, similar to the way you wound use the release liner on a Band-Aid bandage.

When using the roller heater system to post the bottom 55 of a formed orthotic 29 the posting layer 50 is heated with Teflon facing up. When heated by any other means than the roller heat system the posting layer 50 should sit on the Teflon. Insert the posting layer 50 into the release liners and then into the roller heat system or heat by other means with the posting layer resting on the release liners. After the posting layer 50 is heated to proper molding temperature, the cooled molded orthotic blank 29 is placed on a flat, heat-resistant surface upside down, so that the cover layer 2 is facing the surface, and the posting layer 50 with heel cutout 18 is facing up. Remove the heated posting layer 50 and the Teflon sheet from the paper silicone liner by holding the edges of the Teflon sheet. With the posting layer 50 still attached to the Teflon sheet, center the cutout 18, 51 of the posting layer 50 over to the cutout 118, 51 of the molded orthotic blank 29. Attach the posting layer 50 to the orthotic heel by massaging the perimeter of the posting layer's edges through the Teflon sheet so the edges are flush and smooth to the molded orthotic 29. Then with the Teflon sheet still attached, quickly turn the orthotic upside down on a flat surface like a table so the posting layer 50 and Teflon sheet 52, 53 are touching the work surface, FIG. 8. The orthotic is now right side up and the posting layer is now facing down. Apply downward pressure to the center of the orthotic heel cup, above the oval cutout for 15 seconds. Turn over orthotic 29 to examine the posting layer 50 and peel the Teflon sheet off. The posting layer 50 will be flat, the orthotic heel cutout 118 will not be filled and the flat zone 18 of the posting layer 50 will prevent the molded orthotic heel from rocking. The material flows into areas as pressure is applied; it will be thick in areas 56 under the least pressure and have thin areas 57 where the most pressure is applied.

It may be difficult to attach the posting layer to the shell layer, especially if the shell layer has been dyed. Adhesion can be enhanced by posting layer 50 being treated with a thinner, acetone, or xylol. After the post is affixed to the insole adhesion can be enhanced by flash cooling the insole and post in cold water.

While specific embodiments of the invention have been shown and described in detail to illustrate the application of the principles of the invention, it will be understood that the invention may be embodied otherwise without departing from such principles.

What is claimed is:

1. A process for forming an orthotic/orthosis for a portion of an individual, the process comprising the steps of:
   providing a cover layer;
   providing a shell layer connected to the cover layer, the shell layer being formed of a thermoplastic having a moldable temperature, the shell layer having a rigidity below the moldable temperature to support the portion of the individual, the shell layer having a flexibility above the moldable temperature to mold the shell layer into a shape to support the portion of the individual, the shell layer being formed from a shell sheet having a thermoplastic ply made of the thermoplastic, the shell sheet is also formed to include a scrim ply embedded in a thermoplastic ply on diametrically opposite sides of the thermoplastic ply;
   connecting the shell layer and the cover layer together to form a blank;
   heating the blank to the moldable temperature;
   placing the heated blank on the portion of the individual;
   molding the heated blank against the portion of individual and into a shape to provide support for the portion of the individual;
   cooling the heated blank while the heated blank is on the portion of the individual and in the shape to provide support, said cooling being performed to below the moldable temperature.

2. A process in accordance with claim 1, wherein:
   the shell layer includes a plurality of the shell sheets;
   said molding of the heated blank includes sliding the plurality of the shell sheets relative to each other as the heated blank is molded against curved surfaces of the portion of the individual and into the shape to provide support for the portion of the individual.

3. A process in accordance with claim 2, wherein:
   said heating of the blank is performed by passing the blank between heated rollers;
   the moldable temperature is in a range of 140-160 degrees Fahrenheit;
   the scrim plies stretch less than the thermoplastic ply.

4. A process in accordance with claim 2, wherein:
   shell sheets closer to the portion of the individual are smaller than shell sheets further away from the portion of the individual.

5. A process in accordance with claim 2, wherein:
   said molding of the heated blank is performed, and the plurality of shell sheets are configured, to form self beveling edges.

6. A process in accordance with claim 1, further comprising:
   providing a posting layer, the posting layer being formed of a posting material having a molding temperature in the range of 140-200 degrees Fahrenheit, the posting material being spreadable to a thickness of 0.002 inches at the molding temperature;
   mounting the posting layer on a side of the shell layer diametrically opposite the cover layer, said mounting of the posting layer occurring after said cooling step.

7. A process in accordance with claim 1, wherein:
   the portion of the individual is a foot;
   said molding is performed around curves on the bottom of the foot.

8. A process in accordance with claim 7, further comprising:
   providing a posting layer with a cutout;
   mounting the posting layer on a side of the shell layer diametrically opposite the cover layer, said mounting of the posting layer occurring after said cooling step, said mounting of the posting layer being performed to arrange the cutout in a heel area of the foot.

9. A process in accordance with claim 1, wherein:
   the shell layer is formed from a shell sheet having a thermoplastic ply made of the thermoplastic, the shell sheet also includes a scrim ply on each diametrically opposite side of the thermoplastic ply, the shell sheet also includes a hot melt adhesive ply on a side of one of the scrim plies diametrically opposite the thermoplastic ply.

10. A process in accordance with claim 1, wherein:
    the thermoplastic includes polycaprolactone and fibers.

11. A process in accordance with claim 1, wherein:
    said connecting of the shell layer and the cover layer is performed through a thermal roller machine and is performed to bevel the edges.

12. A process for forming an orthotic/orthosis for a portion of an individual, the process comprising the steps of:
    providing a cover layer;
    providing a shell layer connected to the cover layer, the shell layer being formed of a thermoplastic having a moldable temperature, the shell layer having a rigidity below the moldable temperature to support the portion of the individual, the shell layer having a flexibility above the moldable temperature to mold the shell layer into a shape to support the portion of the individual;
connecting the shell layer and the cover layer together to form a blank;
heating the blank to the moldable temperature;
placing the heated blank on the portion of the individual;
molding the heated blank against the portion of individual and into a shape to provide support for the portion of the individual;
cooling the heated blank while the heated blank is on the portion of the individual and in the shape to provide support, said cooling being performed to below the moldable temperature;
providing a posting layer, the posting layer being formed of a posting material having a molding temperature in the range of 140-200 degrees Fahrenheit, the posting material being spreadable to a thickness of 0.002 inches at the molding temperature;
mounting the posting layer on a side of the shell layer diametrically opposite the cover layer, said mounting of the posting layer occurring after said cooling step.

13. A process in accordance with claim 12, further comprising:
forming the posting layer to define a cutout in an area of an apex of the portion of the individual.

14. A process in accordance with claim 12, wherein:
said mounting of the posting layer is performed with the posting layer at the molding temperature.

15. A process in accordance with claim 14, wherein:
the portion of the individual is a foot;
said molding is performed around curves on the bottom of the foot;
the posting layer is provided with a cutout;
said mounting of the posting layer is performed with the cutout adjacent a sensor of the heel of the foot;
said mounting of the posting layer is performed to have the posting layer be thinner in the area of the cutout;
said mounting of the posting layer being performed, and the posting material being configured to be self beveling.

16. A process in accordance with claim 12, wherein:
said mounting of the posting layer is performed by massaging edges of the posting layer be flush and smooth to the blank;
said mounting of the posting layer is performed by pressing a side of the posting diametrically opposite the blank against a flat surface.

17. A process in accordance with claim 12, wherein:
said molding of the heated blank forms the shell layer with a curved surface having an apex curving outward on the side of shell layer facing the posting layer;
a reinforcing stabilizer layer is arranged between the shell layer and the posting layer, the reinforcing stabilizer layer being formed of materials similar to materials of the shell layer, the reinforcing stabilizer layer defining a cutout portion in a heel area of the foot;
the posting layer defines a cutout portion in a heel area of the foot, the cutout portion of the posting layer being larger than the cutout portion of the reinforcing stabilizer layer, the cutout areas of the posting layer and the reinforcing stabilizer layer cooperating with the curved surface of the shell layer to form a flat surface on a side of the orthotic/orthosis diametrically opposite the cover layer.

18. A process for forming an orthotic/orthosis for a portion of an individual, the process comprising the steps of:
providing a cover layer;
providing a shell layer connected to the cover layer, the shell layer being formed of a thermoplastic having a moldable temperature, the shell layer having a rigidity below the moldable temperature to support the portion of the individual, the shell layer having a flexibility above the moldable temperature to mold the shell layer into a shape to support the portion of the individual;
connecting the shell layer and the cover layer together to form a blank;
heating the blank to the moldable temperature;
placing the heated blank on the portion of the individual;
molding the heated blank against the portion of individual and into a shape to provide support for the portion of the individual;
cooling the heated blank while the heated blank is on the portion of the individual and in the shape to provide support, said cooling being performed to below the moldable temperature;
the portion of the individual being a foot;
said molding being performed around curves on the bottom of the foot;
providing a posting layer with a cutout;
mounting the posting layer on a side of the shell layer diametrically opposite the cover layer, said mounting of the posting layer occurring after said cooling step, said mounting of the posting layer being performed to arrange the cutout in a heel area of the foot.

19. A process for forming an orthotic/orthosis for a portion of an individual, the process comprising the steps of:
providing a cover layer;
providing a shell layer connected to the cover layer, the shell layer being formed of a thermoplastic having a moldable temperature, the shell layer having a rigidity below the moldable temperature to support the portion of the individual, the shell layer having a flexibility above the moldable temperature to mold the shell layer into a shape to support the portion of the individual;
connecting the shell layer and the cover layer together to form a blank;
heating the blank to the moldable temperature;
placing the heated blank on the portion of the individual;
molding the heated blank against the portion of individual and into a shape to provide support for the portion of the individual;
cooling the heated blank while the heated blank is on the portion of the individual and in the shape to provide support, said cooling being performed to below the moldable temperature;
the shell layer being formed from a shell sheet having a thermoplastic ply made of the thermoplastic, the shell sheet also includes a scrim ply on each diametrically opposite side of the thermoplastic ply, the shell sheet also includes a hot melt adhesive ply on a side of one of the scrim plies diametrically opposite the thermoplastic ply.

20. A process for forming an orthotic/orthosis for a portion of an individual, the process comprising the steps of:
providing a cover layer;
providing a shell layer connected to the cover layer, the shell layer being formed of a thermoplastic having a moldable temperature, the shell layer having a rigidity below the moldable temperature to support the portion of the individual, the shell layer having a flexibility above the moldable temperature to mold the shell layer into a shape to support the portion of the individual;
connecting the shell layer and the cover layer together to form a blank;
heating the blank to the moldable temperature;
placing the heated blank on the portion of the individual;
molding the heated blank against the portion of individual and into a shape to provide support for the portion of the individual;
cooling the heated blank while the heated blank is on the portion of the individual and in the shape to provide support, said cooling being performed to below the moldable temperature;
said connecting of the shell layer and the cover layer being performed through a thermal roller machine and is performed to bevel the edges.

* * * * *